United States Patent
Lam et al.

(10) Patent No.: US 8,758,807 B2
(45) Date of Patent: Jun. 24, 2014

(54) PRESSURE SENSITIVE ADHESIVE COMPOSITION COMPRISING SALT

(75) Inventors: Peter Kwok Hing Lam, Frederiksberg (DK); Anders Bach, Copenhagen (DK); Mads Lykke, Broenshoej (DK); Astrid Toftkaer, Soeborg (DK); Hasse Buus, Humlebaek (DK); Tom Kongebo, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 1303 days.

(21) Appl. No.: 12/448,470

(22) PCT Filed: Dec. 20, 2007

(86) PCT No.: PCT/DK2007/050199
§ 371 (c)(1),
(2), (4) Date: Dec. 10, 2009

(87) PCT Pub. No.: WO2008/074333
PCT Pub. Date: Jun. 26, 2008

(65) Prior Publication Data
US 2010/0113999 A1    May 6, 2010

(30) Foreign Application Priority Data

Dec. 20, 2006 (DK) .................................. 2006 01673
Jul. 6, 2007 (DK) .................................. 2007 01003

(51) Int. Cl.
*A61F 13/02* (2006.01)
(52) U.S. Cl.
USPC ............................................. 424/448; 524/394
(58) Field of Classification Search
USPC ............ 602/42, 52, 54, 57; 424/448; 524/394
See application file for complete search history.

(56) References Cited

U.S. PATENT DOCUMENTS

| | | | |
|---|---|---|---|
| 3,844,865 A | 10/1974 | Elton et al. | |
| 4,650,817 A * | 3/1987 | Allen et al. | 523/105 |
| 4,657,986 A * | 4/1987 | Isayama et al. | 525/407 |
| 4,904,732 A * | 2/1990 | Iwahara et al. | 525/100 |
| 5,049,387 A * | 9/1991 | Amkraut | 424/435 |
| 5,133,821 A | 7/1992 | Jensen | |
| 5,147,339 A * | 9/1992 | Sundstrom | 604/307 |
| 5,387,450 A * | 2/1995 | Stewart | 428/40.4 |
| 6,225,401 B1 * | 5/2001 | Rehmer et al. | 524/800 |
| 6,248,915 B1 | 6/2001 | Ito et al. | |
| 6,451,883 B1 | 9/2002 | Chen et al. | |
| 6,583,220 B1 | 6/2003 | Lipman | |

(Continued)

FOREIGN PATENT DOCUMENTS

CN   1298432 A   6/2001
CN   1454274 A   11/2003

(Continued)

OTHER PUBLICATIONS

Main, K., et al. "Influence of sex and growth hormone deficiency on sweating," Scand J. Clin Lab Invest; 51: pp. 475-480, 1991.

*Primary Examiner* — Patricia Bianco
*Assistant Examiner* — Camtu Nguyen
(74) *Attorney, Agent, or Firm* — Coloplast Corp., Coloplast A/S; Nick Baumann

(57) ABSTRACT

The present invention relates to a pressure sensitive adhesive composition comprising a continuous phase and a discontinuous phase wherein
a) the continuous phase comprises a water vapor permeable hydrophobic polymer; and
b) the discontinuous phase comprises a water soluble salt.

15 Claims, 2 Drawing Sheets

(56) References Cited

U.S. PATENT DOCUMENTS

| | | | |
|---|---|---|---|
| 6,977,323 B1 * | 12/2005 | Swenson | 602/46 |
| 7,446,158 B2 * | 11/2008 | Okamoto et al. | 526/279 |
| 2004/0241246 A1 | 12/2004 | Lipman | |
| 2008/0311396 A1 | 12/2008 | Hamada et al. | |

FOREIGN PATENT DOCUMENTS

| | | |
|---|---|---|
| EP | 0 264 299 A2 | 4/1988 |
| JP | 2002-224706 A | 8/2002 |
| JP | 2004 067720 A | 3/2004 |
| WO | WO 95/05138 | 2/1995 |
| WO | WO 99/54422 A1 | 10/1999 |
| WO | WO 01/32796 A1 | 5/2001 |
| WO | WO 02/33172 A1 | 4/2002 |
| WO | WO 03/062343 A1 | 7/2003 |
| WO | WO 2004/080499 A1 | 9/2004 |
| WO | WO 2005/032401 A3 | 4/2005 |
| WO | WO 2008/028494 * | 3/2008 |

* cited by examiner

PRESSURE SENSITIVE ADHESIVE COMPOSITION COMPRISING SALT

This is a national stage of PCT/DK07/050,199 filed Dec. 20, 2007 and published in English, which has a priority of Denmark no. PA 2006 01673 filed Dec. 20, 2006 and Denmark no. PA 2007 01003 filed Jul. 6, 2007, hereby incorporated by reference.

FIELD OF INVENTION

The invention relates to a novel absorbing pressure sensitive adhesive composition comprising salt, and medical devices comprising said absorbing adhesive composition.

BACKGROUND

Pressure sensitive adhesives have for a long time been used for attaching medical devices, such as ostomy appliances, dressings (including wound dressings), wound drainage bandages, devices for collecting urine, orthoses and prostheses to the skin.

It has been reported that humans for short periods can sweat more than 20,000 g/m2/24 h, (Main, K., K. O. Nilsson, and N. E. Skakkebaek, 1991, Influence of sex and growth hormone deficiency on sweating, Scand. J. Clin. Lab Invest 51:475-480).

Thus, the moisture handling ability of skin contact adhesives, i.e. both the water absorption capacity and the moisture vapour transmission rate of the adhesive, is important.

When designing a skin adhesive one of the major issues is to keep the skin relatively dry underneath the adhesive to prevent maceration. Maceration occurs when skin is unable to get rid of moisture from transpiration and results in degradation of the skin barrier function.

Usually, skin adhesive keeps the skin dry by being water permeable. This allows moisture to transport through the adhesive from the skin side to the outer side, where it is allowed to evaporate. This mechanism is not usable for ostomy skin adhesives because a water impermeable layer covers the outer side of an ostomy adhesive. The water impermeable layer prevents ostomy discharge to enter the adhesive from the outside. Thus, evaporation of moisture is not possible. Hence, adhesive compositions used for ostomy appliances are made water absorbent. Absorbing particles or hydrocolloids (HC) are mixed into a hydrophobic adhesive matrix to absorb moisture from the skin and thereby keeping the skin relatively dry. This technique is well known in the art (see for example U.S. Pat. No. 6,451,883) and forms the basis for all commercially available ostomy adhesives.

The adhesive matrix in traditional, state of the art of ostomy adhesives without HC particles is very hydrophobic with very low water permeability. The only way water can transmit within the adhesive is through the hydrocolloid particles that are mixed therein. As these particles are much smaller than the total thickness of the adhesive layer, the only way water can migrate into the adhesive is if the HC particles touch each other and form bridges for water to permeate through. This limit in water transportation dictates a relatively high loading of hydrocolloid particles in the adhesive such that enough particles touch each other. As the particles used are hard relative to the adhesive matrix, this addition of a large quantity of particles makes the adhesive hard and uncomfortable for the user.

By using a water permeable adhesive matrix such as the adhesive described in WO 05/032401 the water transportation is less dependent on the number of particles that touches each other, fewer particles are needed to ensure proper water mobility in the adhesive.

Unfortunately, by reducing the amount of absorbing particles, the absorption capacity and rate is reduced. Water absorption in the adhesive is driven by a difference in vapour pressure between the skin and the inside of the adhesive. The vapour pressure over hydrocolloids grows rapidly towards the equilibrium vapour pressure of water as water is absorbed by the particles. As vapour pressure grows in the hydrocolloids, the driving force reduces and water transport gets slower. This would also be the case for a regular HC adhesive with impermeable adhesive matrix, but here, water transport is helped by the expanding particles starting to touch more neighbour particles and form more bridges. This way the resistance against water flux reduces and compensates for the lower driving force.

Thus, reducing the amount of particles not only reduces the absorption capacity but also reduces the absorption rate of the adhesive. Using the known technology today, it is not possible to make an ostomy adhesive that is soft, have high water absorption capacity and also have a relatively high and constant transient water uptake.

The present invention provides an absorbing adhesive with very low particle loading and still having high water absorption capacity.

SUMMARY OF THE INVENTION

Accordingly, the present invention relates to a pressure sensitive adhesive composition comprising a continuous phase and a discontinuous phase wherein
  a) the continuous phase comprises a water vapour permeable hydrophobic polymer; and
  b) the discontinuous phase comprises a water soluble salt.

DETAILED DESCRIPTION OF THE INVENTION

Figure 1:
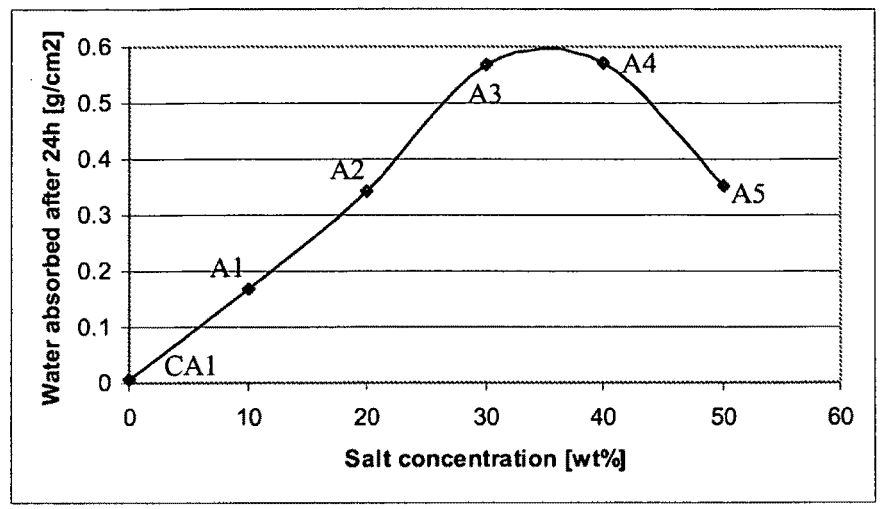
FIG. 1 shows the weight gain of adhesives after 24 h in saline water. Adhesives CA1 and A1-A5 are plotted as function of NaCl content.

The present invention relates to a pressure sensitive adhesive composition comprising a continuous phase and a discontinuous phase wherein
  a) the continuous phase comprises a water vapour permeable hydrophobic polymer; and
  b) the discontinuous phase comprises a water soluble salt.

As used herein, the total adhesive composition means the discontinuous phase and the continuous phase in combination.

As used herein the discontinuous phase means the salt(s) or mixture of salts and any other solid materials, preferably in particulate form, such as filler (native starch), colours, hydrocolloids etc which are distributed in the continuous phase.

As used herein the continuous phase means the total adhesive composition except the discontinuous phase.

The present invention provides an absorbing adhesive with very low particle loading and still high water absorption capacity. These very attractive features are obtained by using water-soluble salt crystals instead of water absorbent particles as absorbers. Furthermore, it is required that the adhesive matrix is water vapour permeable and ion impermeable. In this way, water vapour can diffuse towards the salt crystal and slowly dissolve it, but the ions from the dissolved salt cannot escape the adhesive matrix.

Usually water soluble salts cannot be used as absorbing particles because upon water contact, they dissolve and will leach out of the polymer matrix.

Surprisingly, the water soluble salt and permeable polymer combination can absorb moisture without the negative effect of the salt solution leaching out. One theory of how this works is that the polymer and salt distribution provide an osmotic effect and moisture is transported through the vapour permeable but liquid impermeable polymer acting as a membrane. The liquid impermeable polymer also has a function of sealing the salt solution in until the pressure balance is changed sufficiently. This, in normal use of these adhesives, is never reached, so the transport is essentially in one direction only. As long as there is no tunnel or opening leading directly to the surfaces of the adhesive, the salt solution cannot leach out.

A salt crystal in an adhesive matrix "absorbs" in a fundamentally different way than a regular hydrocolloid in an adhesive matrix:

First, the amount of water that a salt crystal can absorb at a given partial pressure of water can be huge compared to the hydrocolloid. For example, at room temperature at 75% relative humidity (RH), ordinary kitchen salt (NaCl) can absorb about 3 times its own weight whereas a hydrocolloid like Aquasorb A800 only absorbs about 0.2 times its own weight. Thus, simple kitchen salt has a water absorption capacity that is an order of magnitude higher than hydrocolloids.

Next, the vapour pressure over a salt particle is independent of the amount of absorbed water until the salt crystal is completely dissolved. This is contradictorily to the hydrocolloid particle where equilibrium vapour pressure increases rapidly with the amount of absorbed water. When the vapour pressure increases, the difference between vapour pressure on the skin and the adhesive is reduced and thus the driving force of water transport is reduced. This difference in the vapour pressure effects makes the absorption rate of an adhesive with salt crystals more constant in time and less a function of the amount of absorbed water.

Finally, the mechanical behaviour of the adhesive also changes during absorption of water. When no water is absorbed in an adhesive with salt crystals in it, the adhesive will be harder than the equivalent adhesive without particles. This is because the crystal particles are harder than the adhesive matrix. However, as the adhesive starts to absorb water, the crystals are dissolved and the adhesive gets softer and softer.

A surprising benefit of the salt turning to liquid form upon dissolution but still being kept in pockets within the polymer matrix, is that the adhesive moduli are reduced. The adhesive becomes softer and even more comfortable to wear. But there is no reduction in erosion resistance From the physics of dissolving salts, it is possible, to a first order approximation, to calculate the minimum solubility of the salt to achieve satisfactory absorption rates. Raoult's law teaches that the equilibrium vapour pressure of a species (in the present case: water) over a solution containing the species is equal to the saturated vapour pressure of the pure species multiplied by its mole fraction in the solution.

$$p_{H_2O} = x_{H_2O} p_{H_2O}^{sat}$$

According to the invention it is desired that the vapour pressure in the particles to be less than 98% of pure water (very close to isotonic water) because a vapour pressure gradient between skin and adhesive is needed to have water transportation into the adhesive. From the minimum vapour pressure requirement according to the invention and Raoult's law it is possible to calculate the minimum salt solubility:

$$0.98 > \frac{p_{H_2O}}{p_{H_2O}^{sat}} = x_{H_2O} = \frac{n_{H_2O}}{n_{H_2O} + n_{salt}}$$

Where $p_{H2O}$ is partial pressure of water, $p_{H2O}^{sat}$ is vapour pressure of pure water, $x_{H2O}$ is the molar fraction of water and $n_{H2O}$ and $n_{salt}$ are molar concentrations of water and salt.

According to this equation the minimum solubility of the salt is calculated to be 1.13 mol/L $H_2O$.

A water soluble salt according to the invention can be an inorganic salt or an organic salt.

As used herein a water soluble inorganic salt means any acidic substance in which two or more chemical elements other than carbon are combined, nearly always in definite proportions, as well as some compounds containing carbon but lacking carbon-carbon bonds (e.g., carbonates, cyanides), where all or part of the hydrogen ions of the acid are replaced with metal ions or electropositive radicals, and the substance is fully soluble at 1 mole per liter or more in water to a clear solution.

According to one embodiment of the invention the water soluble salt is fully soluble at 1 mole per liter.

As used herein a water soluble organic salt means the reaction product of an organic acid and a base, for example, sodium acetate ($CH_3COONa$) from the reaction of acetic acid ($CH_3COOH$) and sodium hydroxide (NaOH) and the substance is fully soluble at 1 mole per liter or more in water to a clear solution.

According to one embodiment of the invention the pressure sensitive adhesive composition comprises inorganic salt.

According to one embodiment of the invention the pressure sensitive adhesive composition comprises water soluble inorganic salt, where the positive ion is any cation preferably from group one, group two, transition metals, aluminium and ammonium.

According to one embodiment of the invention the pressure sensitive adhesive composition comprises water soluble inorganic salt from the group of but not limited to NaCl, $CaCl_2$, $K_2SO_4$, $NaHCO_3$, $Na_2CO_3$, KCl, NaBr, NaI, KI, $NH_4Cl$, $AlCl_3$ and mixtures thereof.

According to a preferred embodiment of the invention the water soluble salt is NaCl.

According to another embodiment of the invention the pressure sensitive adhesive composition comprises organic salt.

According to one embodiment of the invention the pressure sensitive adhesive composition comprises water soluble organic salt from the group of but not limited to $CH_3COONa$, $CH_3COOK$, COONa, COOK and mixtures thereof.

According to one embodiment of the invention the salt content of the water soluble salt is below 40 wt % of the total pressure sensitive adhesive composition.

According to one embodiment of the invention the pressure sensitive adhesive composition comprises water vapour permeable hydrophobic polymer from the group of but not limited to polypropyleneoxide, polyurethane, silicone, polyacrylic or ethylene vinyl acetate and mixtures thereof.

As used herein a water vapour permeable hydrophobic polymer means a polymer that absorbs less than 5% in wt, preferably less than 1%, at equilibrium and has a moisture vapour transmission rate of greater than 20 g/m2/24 hrs, preferably greater than 100 g/m2/24 hrs.

In one embodiment of the invention the water vapour permeable hydrophobic polymer is crosslinked.

As used herein a crosslink means a small region in a macromolecule (polymer chain structure) from which more than 2 chains emanate. The linking may be covalent, physical or ionic.

In another embodiment of the invention the water vapour permeable hydrophobic polymer has a permeability above 20 g/m²/24 h.

In another embodiment of the invention the water vapour permeable hydrophobic polymer is a block copolymer.

As used herein a block copolymer means a copolymer in which the repeating units in the main chain occur in blocks, eg, -(a)m-(b)n-(a)p-(b)q-, where a and b represent the repeating units.

In a preferred embodiment of the invention the water vapour permeable hydrophobic polymer is polypropyleneoxide.

In a preferred embodiment of the invention the water vapour permeable hydrophobic polymer is polyurethane.

In a preferred embodiment of the invention the water vapour permeable hydrophobic polymer is silicone.

In a preferred embodiment of the invention the water vapour permeable hydrophobic polymer is polyacrylic.

In a preferred embodiment of the invention the water vapour permeable hydrophobic polymer is ethylene vinyl acetate.

Preferred particle size of the discontinuous phase is as small as possible, smaller particles are more difficult to see by the naked eye and will give products that are more pleasing to the eye. An upper limit on particle size is the size of the smallest dimension of the adhesive. Thus, a 300 μm thick adhesive should not contain particles with diameters above 300 μm. There is a tendency of the hygroscopic particles to agglomerate and this effect will increase with decreasing particle size. Therefore, a preferred particle size would be from 10-300 μm. Also, the particles may contain an anti agglomerating agent to reduce agglomeration of small particles.

According to one embodiment of the invention the water vapour permeable hydrophobic polymer comprises the reaction product of:

(i) a polyalkyleneoxide polymer having one or more unsaturated end groups, and (ii) an organosiloxane comprising one or more Si—H groups, carried out in the presence of an addition reaction catalyst.

According to another embodiment of the invention the pressure sensitive adhesive composition comprises more than 90% w/w of the polyalkylene oxide polymer that consist of polymerised alkyleneoxide moities having three or more carbon atoms.

According to another embodiment of the invention, the adhesive composition comprises the reaction product of:

(i) a polyalkyleneoxide polymer having at least two unsaturated end groups, and wherein more than 90% w/w of the polyalkylene oxide polymer consist of polymerised alkyleneoxide moities having three or more carbon atoms, (ii) a polysiloxane cross-linking agent comprising 3 or more Si—H groups and optionally (iii) a polysiloxane chain extender comprising up to 2 Si—H groups carried out in the presence of an addition reaction catalyst.

According to a preferred embodiment of the invention the addition reaction catalyst is a Pt vinyl siloxane complex.

According to a preferred embodiment of the invention the polyalkylene oxide polymer is polypropyleneoxide.

According to a further preferred embodiment of the invention the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention the polyalkylene oxide polymer is polypropyleneoxide.

The polypropylene oxide having unsaturated end groups may be a compound of formula

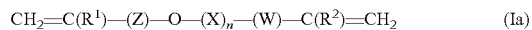

$$CH_2=C(R^1)—(Z)—O—(X)_n—(W)—C(R^2)=CH_2 \quad (Ia)$$

or

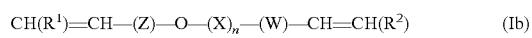

$$CH(R^1)=CH—(Z)—O—(X)_n—(W)—CH=CH(R^2) \quad (Ib)$$

wherein $R^1$ and $R^2$ are independently selected from hydrogen and $C_{1-6}$-alkyl;

Z and W is $C_{1-4}$-alkylene;

X is —$(CH_2)_3$—O— or —$CH_2$—$CH(CH_3)$—O—; and n is 1-900, more preferred 10-600, or most preferred 20-600.

The number average molecular weight of the polyalkylene oxide having unsaturated end groups is suitably between 500 and 100000, more preferred between 500 and 50,000 and most preferred between 1000 and 35,000.

Polypropylene oxide having unsaturated end groups may be prepared as described in U.S. Pat. No. 6,248,915 and WO 05/032401 or analogously to the methods described therein. Other polyalkylene oxide polymers may be prepared analogously.

The polysiloxane cross-linking agent comprising 3 or more Si—H groups is suitable a compound having the formula

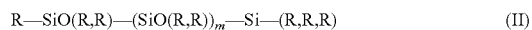

$$R—SiO(R,R)—(SiO(R,R))_m—Si—(R,R,R) \quad (II)$$

wherein at least three of the groups R is hydrogen and the rest of the groups R are each independently selected from $C_{1-12}$-alkyl, $C_{3-8}$-cycloalkyl, $C_{6-14}$-aryl, and $C_{7-12}$-arylalkyl; and m is 5-50, or preferably 10-40. The number average molecular weight as determined by GPC is suitably 500-3000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula

$$R^3—SiO(R^3,R^3)—(SiO(R^3,R^3))_m—Si—(R^3,R^3,R^3) \quad (III)$$

wherein up to 2 of the groups $R^3$ is hydrogen and the rest of the groups $R^3$ are each independently selected from $C_{1-12}$-alkyl, $C_m$-cycloalkyl, $C_{6-14}$-aryl, and $C_{7-12}$-arylalkyl; and m is 0-50. The number average molecular weight as determined by GPC is suitably between 200 and 65000, most preferably between 200 and 17500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the —$(SiO(R^3,R^3))_m$— chain of the compound of formula (II).

The polysiloxane cross-linking agent and the chain extender may be prepared as described in Japanese Patent Application 2002-224706 and WO 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxan and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w, and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The pressure sensitive adhesive composition according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, surfactants. The adhesive may also comprise pharmaceutically active ingredients. These optional ingredients may be present in the reaction mixture during the cross linking reaction.

In one embodiment of the invention the pressure sensitive adhesive composition comprising a continuous phase and a discontinuous phase wherein a) the continuous phase is water vapour permeable and hydrophobic; and b) the discontinuous phase comprises a water soluble salt.

In a preferred embodiment of the invention the water vapour permeable and hydrophobic continuous phase comprises a polymer as described above.

In one embodiment of the invention the pressure sensitive adhesive composition further comprises hydrocolloid.

In a preferred embodiment of the invention the amount of hydrocolloid is below 50% w/w of the total composition.

In another embodiment of the invention a layered adhesive construct comprising a backing layer and at least one layer of a pressure sensitive adhesive composition according to the invention.

The invention may be foamed into foamed adhesive in a number of ways, either chemically or mechanically.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilisation of low boiling materials or by a combination of these methods.

Any of the commercially known chemical blowing agents may be used. The chemical blowing agents is suitably non-toxic, skin friendly, and environmentally safe, both before and after decomposition.

The amount of chemical blowing agent to be added to the adhesive mixture may range from about 0.01% up to about 90% by weight, with a practical range including about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process.

Another method for creating a foamed adhesive of the invention is a method where a mechanical process is used to add a physical blowing agent, similar to whipping the adhesive mass into froth, thus creating a foamed structure. Many processes are possible including processes involving incorporation of air, nitrogen, carbon dioxide, or other gases or low boiling point volatile liquids during the manufacturing process for the adhesive.

The invention also relates to medical devices comprising a pressure sensitive adhesive composition as described above.

The medical device comprising an adhesive composition according to the invention may be an ostomy appliance, a dressing (including wound dressings), a wound drainage bandage, a skin protective bandage, a device for collecting urine, an orthose or a prosthese, e.g. a breast prothesis, and electronic device such as a measuring instrument or a power source, such as a battery.

The medical device may also be a tape (e.g an elastic tape or film), or a dressing or a bandage, for securing a medical device, or a part of the medical device to the skin, or for sealing around a medical device attached to the skin.

The medical device may in its simplest construction be an adhesive construction comprising a layer of the pressure sensitive adhesive composition according to the invention and a backing layer.

The backing layer is suitably elastic (have a low modulus), enabling the adhesive construction to conform to the skin movement and provide comfort when using it.

The thickness of the backing layer used according to the invention is dependent on the type of backing used. For polymer films, such as polyurethane films, the overall thickness may be between 10 to 100 µm, preferably between 10 to 50 µm, most preferred about 30 µm.

In one embodiment of the invention the backing layer is non-vapour permeable.

In another embodiment of the invention the backing layer is water vapour permeable and have a moisture vapour transmission rate above 500 g/m$^2$/24 h. In this case the adhesive construction of the invention may provide a good moisture absorption rate and absorption capacity and is able to transport a large quantity of moisture through the construction and away from the skin. Both the chemical composition and physical construction of the adhesive layer and the chemical and physical construction of the backing layer affect the water vapor permeability. With regard to the physical construction, the backing layer may be continuous (no holes, perforations, indentations, no added particles or fibers affecting the water vapor permeability) or discontinuous (it has holes, perforations, indentations, added particles or fibers affecting the water vapor permeability).

The moisture vapour transmission rate of the backing layer is suitably above 500 g/m$^2$/24 h, most preferably above 1000 g/m$^2$/24 h, even more preferred above 3000 and most preferred above 10,000.

The adhesive composition according to the invention is suitable for fastening a prosthetic device to the skin. For example breast prosthesis could be fastened using adhesives described in this patent. The adhesive composition according to the invention is superior to state of the art because it can keep the skin dry by absorbing moisture.

The adhesive composition is completely elastic in its nature. It only absorbs water and no absorbent is allowed to leak out. Thus, deformations are reversible through the elasticity of the adhesive and water absorption is reversible by drying. The adhesive composition according to the invention is therefore very suitable as a reusable adhesive.

An ostomy appliance of the invention may be in the form of an adhesive wafer forming part of a two-piece appliance or in the form of a one-piece appliance comprising a collecting bag for collecting the material emerging from the stoma and an adhesive flange for attaching the one-piece appliance to the skin of the ostomate. A separate collecting bag may be attached to the adhesive wafer by any manner known per se, e.g. through mechanical coupling using a coupling ring or through use of adhesive flanges. The adhesive according to this invention may be one of more layers that make up the total adhesive sheet.

In another embodiment of the invention, the adhesive is part of a faecal-collecting device, attaching a bag or another collecting device to the perianal skin.

A dressing or adhesive sheet of the invention may have beveled edges in order to reduce the risk of "rolling-up" the edge of the dressing reducing the wear-time. A beveling may be carried out discontinuously or continuously in a manner known per se e.g. as disclosed in EP Patent No. 0 264 299 or U.S. Pat. No. 5,133,821

EXPERIMENTAL

The following materials were used to prepare pressure sensitive adhesives according to the invention and pressure sensitive adhesive compositions for comparison:

ACX003, allyl-terminated polyether (poly propylene oxide) viscosity 16 Pa·s from Kaneka.

Catalyst, Pt-VTS. Pt-VTS is Pt-divinyl teteramethyl disiloxane in IPA (Pt 3.0 wt %).

CR600, poly-alkyl hydrogen siloxane curing agents available from Kaneka.

Kraton 1107 (Kraton) SIS, Styrene 15%.

Arkon P115: A saturated alicyclic hydrocarbon resin from Arakawa Chemical Industries.

DOA: Dioctyl adipate, a plasticizer from International Speciality Chemicals Ltd.

Gelva GMS2853 acrylic copolymer from Cytec Surface specialties Nordic A/S

Polyol: 14944-44 H dev. polyol from DOW.

Vorastar: Isocyanate, HB6013 from DOW.

Silicone A: Dow Croning 7-9677 Part A

Silicone B: Dow Croning 7-9677 Part B

PU film: BL9601, Intellicoat. MWTR=10000 g/m$^2$/24 h

Methods

Determination of Moisture Vapour Transmission Rate (MVTR)

MVTR is measured in grams per square meter (g/m$^2$) over a 24 hours period using an inverted cup method.

A container or cup that is water and water vapour impermeable having an opening is used. 20 ml saline water (0.9% NaCl in demineralised water) is placed in the container and the opening is sealed with the test adhesive film. The container, with a duplicate, is placed into an electrically heated humidity cabinet and the container or cup is placed up side down such that the water is in contact with the adhesive. The cabinet is maintained at 37° C. and 15% relative humidity (RH). After about an hour, the containers are considered to be in equilibrium with the surroundings and it is weighed. 24 h after the first weighing, the containers are weighed again. The difference in weight is due to evaporation of vapour transmitted through the adhesive film. This difference is used to calculate Moisture vapour transmission rate or MVTR. MVTR is calculated as the weight loss after 24 h divided by the area of the opening in the cup (g/m$^2$/24 h). The MVTR of a material is a linear function of the thickness of the material. Thus, when reporting MVTR to characterize a material, it is important to inform the thickness of the material which MVTR is reported. We use 150 µm as a reference. If thinner or thicker samples have been measured, the MVTR is reported as corresponding to a 150 µm sample. Thus a 300 µm sample with a measured MVTR of 10 g/m$^2$/24 h is reported as having MVTR=20 g/m$^2$/24 h for a 150 µm sample because of the linear connection between thickness of sample and MVTR of sample. Finally, we note that by using this method, we introduce an error by using a supporting PU film. However, the water permeability of the used film is very high (10000 g/m$^2$/24 h) and the error that is introduced is very small.

Determination of Water Absorption

Pieces of adhesive of 1×25×25 mm$^3$ were immersed in saline water (0.9% NaCl in demineralised water) at 37° C. The samples was removed and carefully dripped dry and weighed after 30, 60, 90, 120, 240, and 1440 hours. The change in weight is recorded and reported as weight gain in g/cm$^2$.

Sample Preparation

Adhesive A1-5 and A2p

Adhesive base: 100 g of adhesive base was produced by mixing polymer AC003, cross-linker CR600 and catalyst in ratios given in the table below.

TABLE 1

Mixing ratios of PPO adhesive base

| | |
|---|---|
| Polymer AC003 batch3076 | 96.45 |
| Cross linker CR600 | 3.45 |
| Catalyst | 0.10 |

To produce samples for water absorption, 20 g adhesive base was transferred to a small beaker and mixed with a precalculated amount of NaCl to produce weight ratios given in Table 2. The slurry was cured between two releaseliners with a 1 mm distance between them to produce an adhesive sheet of 1 mm thickness.

Adhesive A2p was produced by coating a PU film (BL9601) with 150 µm thick adhesive layer and curing the adhesive at 100° C. for 1 hour.

Comparative Adhesive CA1

25 g of adhesive base from A1-A5 were cured between two pieces of release liners with a 1 mm distance between them to produce an adhesive sheet of 1 mm thickness.

Comparative Adhesive CA2 and CA2p

First an adhesive base was mixed (SIS adhesive): Kraton 1107 (15 g), Arkon P115 (25 g) and DOA oil (5 g) were mixed in a Z Mixer for 40 minutes at 140° C. under a vacuum of 100 mbar. 10 g of this adhesive was removed and 8.75 g NaCl was added and mixing was continued for 10 min.

CA2p was produced by pressing adhesive without NaCl between a releaseliner and a PU film (BL9601). The adhesive thickness was 300 µm.

CA2 was produced by compression moulding the adhesive mass containing salt between two releaseliners with a 1 mm distance between them to produce an adhesive sheet of 1 mm thickness.

Adhesive A9-12 and Comparative Adhesive CA3

An adhesive base as the one prepared for adhesive A1-A5 was produced. 20 g of the base material was mixed with 5.0 g of either a salt (A9-12) or Silica gel (CA3). The slurry was cured between two releaseliners with a 1 mm distance between them to produce an adhesive sheet of 1 mm thickness.

Adhesive A6 and A6p

A PU adhesive was prepared by mixing 100.0 g of polyol (14944-44 H dev. polyol from DOW) and 23.5 g of an isocyanate (Vorastar HB6013 from DOW). The components were mixed thoroughly by hand.

To produce A6p, some of this adhesive was coated on a PU film (BL9601) with very high water permeability. Coating thickness of the adhesive was 150 µm.

A6 was produced from the remaining adhesive; 20 g was transferred to a small beaker and mixed with 5.0 g NaCl. The slurry was cured between two releaseliners with a 1 mm distance between them to produce an adhesive sheet of 1 mm thickness. Curing was rather slow and had to be performed in a rotary oven to prevent sedimentation of the salt particles.

Adhesive A7 and A7p

A Silicone adhesive was prepared by mixing 50.0 g of Silicone A and 50.0 g of Silicone B. The components were mixed thoroughly by hand.

To produce A7p, some of this adhesive was coated on a PU film (BL9601) with very high water permeability. Coating thickness of the adhesive was 150 µm.

A7 was produced from the rest; 20 g was transferred to a small beaker and mixed with 5.0 g NaCl. The slurry was cured between two releaseliners with a 1 mm distance between them to produce an adhesive sheet of 1 mm thickness.

Adhesive A8 and A8p 200 g of an acrylic adhesive was mixed containing 35% Gelva GMS2853 and 65% Ethylacetate. To produce A8p, some of this adhesive was coated on a PU film (BL9601) with very high water permeability. After coating, the solvents were allowed to evaporate leaving behind only a layer of polymers. Final coating thickness of the adhesive was 340 µm.

A8 was produced from the rest; 60 g was transferred to a small beaker and mixed with 5.25 g NaCl. The slurry was 'cured' by evaporation of solvent, leaving behind 21 g of polymer and 5.25 g NaCl (20% salt NaCl by weight). 1 mm thick adhesives were produced for water absorption tests.

Prepared samples are tabulated below in terms of their weight percent content.

TABLE 2

Permeable adhesives with different amounts of absorbing particles

| | CA1 | A1 | A2 | A3 | A4 | A5 |
|---|---|---|---|---|---|---|
| PPO adhesive | 100.0 | 90.0 | 80.0 | 70.0 | 60.0 | 50.0 |
| NaCl | 0 | 10.0 | 20.0 | 30.0 | 40.0 | 50.0 |

TABLE 3

Adhesives with different permeability and same amount of salt

| | CA2 | A2 | A6 | A7 | A8 |
|---|---|---|---|---|---|
| SIS adhesive | 80.0 | | | | |
| PPO adhesive | | 80.0 | | | |
| PU adhesive | | | 80.0 | | |
| Silicone adhesive | | | | 80.0 | |
| Acrylic adhesive | | | | | 80.0 |
| NaCl | 20.0 | 20.0 | 20.0 | 20.0 | 20.0 |

TABLE 4

Adhesives for testing water vapour permeability of the adhesive matrix

| | CA2p | A2p | A6p | A7p |
|---|---|---|---|---|
| SIS adhesive | 100 | | | |
| PPO adhesive | | 100 | | |
| PU adhesive | | | 100 | |
| Silicone adhesive | | | | 100 |

TABLE 5

Permeable adhesive with different absorbing particles

| | CA3 | A2 | A9 | A10 | A11 | A12 |
|---|---|---|---|---|---|---|
| PPO adhesive | 80.0 | 80.0 | 80.0 | 80.0 | 80.0 | 80.0 |
| Silica gel | 20.0 | | | | | |
| NaCl | | 20.0 | | | | |
| $CaCl_2 \cdot 2H_2O$ | | | 20.0 | | | |
| $K_2SO_4$ | | | | 20.0 | | |
| KAc | | | | | 20.0 | |
| $NaHCO_3$ | | | | | | 20.0 |

Effect of Salt Concentration

To investigate the effect of salt concentration, a water absorption experiment was set up for samples A1-A5 and CA1 for comparison. Results are presented below in terms of water absorbed after 24 hours submersion in saline water. Some salt must have washed out of the adhesive, reducing the amount of weight gain for high salt loadings. From FIG. 1, we see that there is no salt present in the adhesive (Comparative adhesive CA1), there is practically no water absorption after 24 h. The concentration curve seems to reach a maximum between 30 and 40 wt %, after which the absorption declines (probably because of salt being washed out because they percolate). This is however not a limitation in total salt content. We could easily imagine a structure where a permeable layer of the adhesive without salt was placed on top of the adhesive, this would prevent salt being washed out but still be permeable for water vapour.

Effect of Adhesive Matrix Water Permeability

Next we examine the effect of the water permeability of the adhesive matrix on the same salt containing adhesives ability to absorb water. First we measure the water permeability of the pure adhesives without salt using the method described earlier. Results are tabulated below

TABLE 6

Effect of adhesive matrix water permeability

| Adhesive matrix | Adhesive thickness | Measured MVTR [g/m²/24 h] | MVTR 150 μm thick equivalent [g/m²/24 h] |
|---|---|---|---|
| CA2p (SIS adhesive) | 300 μm | 10 | 20 |
| A2p (PPO adhesive) | 150 μm | 1200 | 1200 |
| A6p (PU adhesive) | 150 μm | 970 | 970 |
| A7p (Silicone adhesive) | 150 μm | 410 | 410 |
| A8p (Silicone adhesive) | 340 μm | 118 | 267 |

Figure 2:
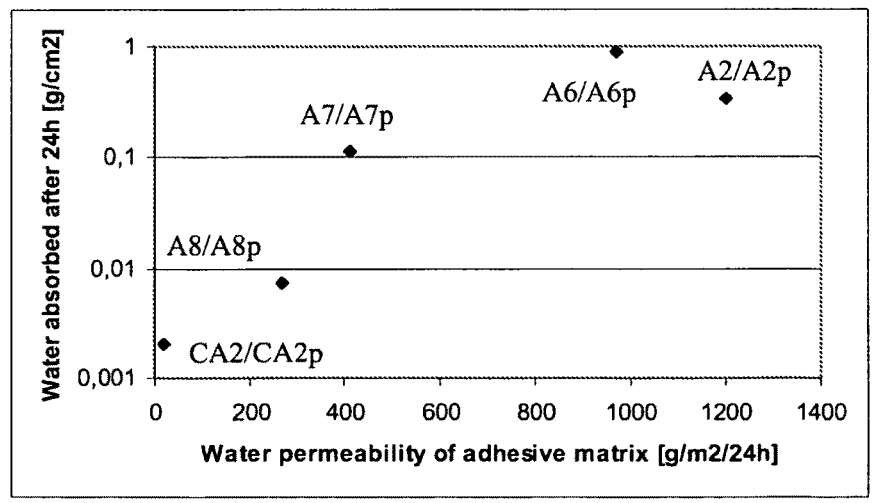
In FIG. 2 water absorption results of adhesives containing 20 wt % NaCl are plotted versus water permeability of the pure adhesive.

Furthermore, water absorption capability of same adhesives containing 20 wt % NaCl was measured in a water absorption experiment. In FIG. 2 water absorption results are plotted versus water permeability of the pure adhesive. FIG. 2 clearly shows that the adhesives A2, A6 and A7 all have relatively high permeability and also good absorption. On the other hand, Comparative adhesive CA2 has low absorption and also relatively low water permeability. Thus, adhesive permeability of at least 20 g/m²/24 h for a 150 μm thick piece of the pure adhesive is required for good water absorption capability. After about 400 g/m²/24 h, the water absorption seems to saturate and the effect of permeability of the pure adhesive has less influence on water absorption capability than at low permeability.

Example 3

Effect of Using Different Salts

Figure 3:
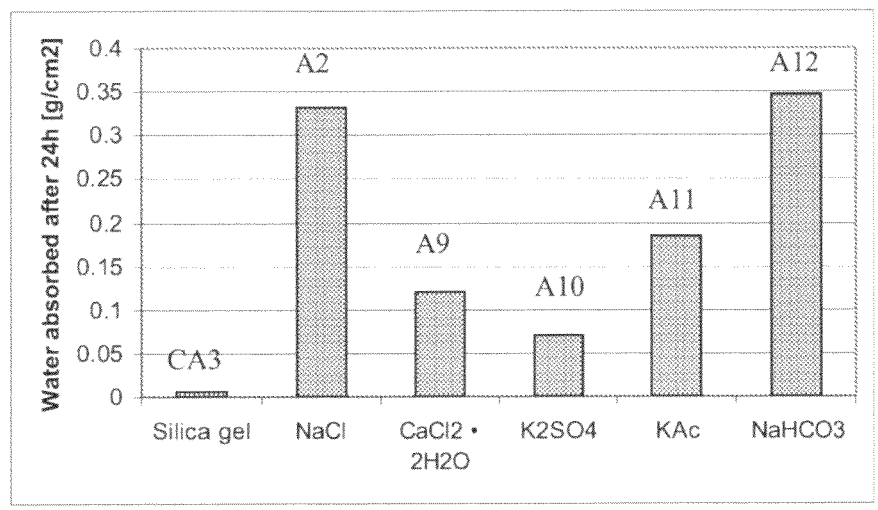
FIG. 3 illustrates the water absorption when using different salts.

Finally, we investigate the water absorption as function of what kind of salt we use. Adhesives A2 and A9-12 all containing the same amount of water soluble salts are compared with Comparative adhesive CA3 containing an insoluble additive (silica gel) proposed in patent application WO95/05138. Absorption after 24 hours are plotted in FIG. 3. We see that adhesives containing water-soluble salts have at least 10 times higher water absorption than the adhesive containing water insoluble salt.

Example 4

EVA Adhesive with Salt

Materials

Levamelt 500, 20 KGy, EVA copolymer, irradiated with 20 KGy Gamma rays, Lanxess, Germany Levamelt 700, 20 KGy, EVA copolymer, irradiated with 20 KGy Gamma rays, Lanxess, Germany Polyglycol B01/120 (PPO), Poly(propylene oxide) oil, Clariant, Germany Pine Crystal, KE311, resin, Hydrogenated rosin ester Arakawa, Japan Suprasel, NaCl, Fine particulate NaCl powder, Akzo Nobel Salt A/S, Denmark Compounding The adhesives were mixed in a Brabender mixer from Brabender OHG, Duisburg, Germany (contains about 60 grams) or a Herrmann Linden LK II 0.5 from Linden Maschinenfabrik, Marienheiden, Germany (contains about 600 grams). The chamber temperature in the mixer was approx 120° C. and the adhesive was compounded with about 50-60 rpm.

Premixtures were made from each polymer. The polymer was added to the mixer and the mixer was started. When the polymer was melted and had a smooth surface, oil was added slowly in small steps, starting with a few ml, followed by increasing amounts. The following part of oil was not added until the previous part was well mixed into the polymer. The ratio between Levamelt and PPO in the premixture was typically approx 1:1.

The adhesives were compounded from the premixtures of polymer and oil. The premixtures were added to the mixer together with resin. The mixer was started, and when the premixture and resin were melted and had a smooth surface, additional oil was added slowly in small steps, starting with a few ml, followed by increasing amounts. Salt was then added to the adhesive and mixing was continued for approx 15 min.

Devices

The resulting adhesives with salt (STR049.2, 4, 5, 6, 7, 8) were thermoformed to an approximately 1 mm thick layer on a soft PU backing.

The same adhesives, but without salt, (STR048.0A & 0B) were thermoformed to approximately 100 micrometer between two release liners.

The non absorbing adhesives were laminated on top of the absorbing adhesives to form the final device.

| | Recipes % (w/w) | | | | | | | |
|---|---|---|---|---|---|---|---|---|
| | STR049.2 | STR049.4 | STR049.5 | Str049.6 | STR049.7 | STR049.8 | STR048.0A | STR048.0B |
| Levamelt 500, 20KGy | 21.4 | 22.6 | 20.2 | 19.0 | 20.5 | 17.8 | 23.8 | 22.7 |
| Levamelt 700, 20KGy | 21.4 | 22.6 | 20.2 | 19.0 | 20.5 | 17.8 | 23.8 | 22.7 |
| PPO B01/120 | 47.3 | 49.9 | 44.6 | 42.0 | 45.2 | 39.4 | 53.0 | 50.0 |
| KE-311 | | | | | 4.3 | | 4.8 | |
| NaCl | 10.0 | 5.0 | 15.0 | 20.0 | 9.6 | 25.0 | | |

Water Absorption

The water permeability of the adhesives without NaCl is about 1000 g/m2/day measured according to the MVTR method.

Water absorption (g/cm2):

| Time (minutes) | Str049.02 + 48.0A | Str049.04 + 48.0A | Str049.05 + 48.0A | Str049.06 + 48.0A | Str049.07 + 48.0B | Str049.08 + 48.0A |
| --- | --- | --- | --- | --- | --- | --- |
| 0 | | | | | | |
| 10 | 0.008 | 0.006 | 0.009 | 0.007 | 0.006 | 0.008 |
| 30 | 0.009 | 0.007 | 0.010 | 0.007 | 0.008 | 0.011 |
| 60 | 0.010 | 0.009 | 0.013 | 0.012 | 0.010 | 0.012 |
| 120 | 0.014 | 0.014 | 0.021 | 0.016 | 0.015 | 0.024 |
| 240 | 0.023 | 0.020 | 0.029 | 0.027 | 0.022 | 0.040 |
| 360 | 0.029 | 0.026 | 0.038 | 0.037 | 0.028 | 0.058 |
| 1440 | 0.070 | 0.057 | 0.096 | 0.105 | 0.068 | 0.173 |

From the measurements it is apparent that good water absorption is achieved over extended periods of time even with as little as 5% (w/w) NaCl

The invention claimed is:

1. A pressure sensitive adhesive composition comprising a continuous phase and a discontinuous phase wherein:
   a) the continuous phase comprises a reaction product of:
      (i) a polyalkyleneoxide polymer having one or more unsaturated end groups, and where more than 90% w/w of the polyalkyleneoxide polymer is polymerised alkyleneoxide moieties having three or more carbon atoms, and
      (ii) an organosiloxane comprising one or more Si—H groups,
   carried out in the presence of an addition reaction catalyst; and
   b) the discontinuous phase comprises a water soluble salt, wherein the water soluble salt is selected from the group consisting of an inorganic salt and an organic salt, the water soluble inorganic salt is selected from the group consisting of NaCl, $CaCl_2$, $K_2SO_4$, $NaHCO_3$, $Na_2CO_3$, KCl, NaBr, NaI, KI, $NH_4Cl$, and mixtures thereof, and the water soluble organic salt is selected from the group consisting of $CH_3COONa$, $CH_3COOK$, COONa, COOK, and mixtures thereof.

2. The pressure sensitive adhesive composition according to claim 1, wherein the reaction product has a permeability above 20 $g/m^2/24$ h.

3. The pressure sensitive adhesive composition according to claim 1, wherein the addition reaction catalyst is a Pt vinyl siloxane complex.

4. The pressure sensitive adhesive composition according to claim 1, wherein the polyalkyleneoxide polymer is polypropyleneoxide.

5. The pressure sensitive adhesive composition according to claim 1, wherein the weight percent of polyalkyleneoxide in said reaction product is 60% or above.

6. The pressure sensitive adhesive composition according to claim 1 wherein the water soluble salt is NaCl.

7. The pressure sensitive adhesive composition according to claim 1, wherein the water soluble salt is fully soluble at 1 mole per liter.

8. The pressure sensitive adhesive composition according to claim 1, wherein the salt content of the water soluble salt is below 40 wt % of the total pressure sensitive adhesive composition.

9. The pressure sensitive adhesive composition according to claim 1, wherein the composition further comprises hydrocolloid.

10. The pressure sensitive adhesive composition according to claim 9, wherein the amount of hydrocolloid is below 50% w/w of the total composition.

11. A layered adhesive construct comprising a backing layer and at least one layer of a pressure sensitive adhesive composition according to claim 1.

12. A medical device comprising a pressure sensitive adhesive composition according to claim 1 and a backing layer.

13. The medical device according to claim 12, wherein the backing layer is non-vapour permeable.

14. The medical device according to claim 12, wherein the backing layer is water vapour permeable and has a moisture vapour transmission rate above 500 $g/m^2/24$ h.

15. The medical device according to claim 12, wherein the medical device is selected from the group consisting of a dressing, an ostomy appliance, a prosthesis, a urine collecting device, a measuring instrument, a therapeutic instrument, a medical tape, and a dressing or bandage for sealing around a medical device on the skin.

* * * * *